United States Patent
Medlock et al.

(10) Patent No.: US 12,090,084 B2
(45) Date of Patent: Sep. 17, 2024

(54) MALE INCONTINENCE DEVICE

(71) Applicants: Michael Medlock, Sanford, FL (US); Faith Medlock, Sanford, FL (US)

(72) Inventors: Michael Medlock, Sanford, FL (US); Faith Medlock, Sanford, FL (US)

(*) Notice: Subject to any disclaimer, the term of this patent is extended or adjusted under 35 U.S.C. 154(b) by 0 days.

(21) Appl. No.: 18/444,920

(22) Filed: Feb. 19, 2024

(65) Prior Publication Data
US 2024/0189138 A1 Jun. 13, 2024

(51) Int. Cl.
A61F 5/453 (2006.01)
A61F 5/44 (2006.01)

(52) U.S. Cl.
CPC ............ *A61F 5/453* (2013.01); *A61F 5/4401* (2013.01); *A61F 5/4408* (2013.01)

(58) Field of Classification Search
CPC ....... A61F 5/453; A61F 5/4401; A61F 5/4408
See application file for complete search history.

(56) References Cited

U.S. PATENT DOCUMENTS

| | | | | |
|---|---|---|---|---|
| 2,310,505 A | * | 2/1943 | Blackburn | A61F 5/453 604/350 |
| 2,445,220 A | * | 7/1948 | Isaacson | A61F 5/4401 604/397 |
| 2,864,369 A | * | 12/1958 | Morrow | A61F 5/4401 604/353 |
| 4,197,849 A | | 4/1980 | Bostick | |
| 4,253,464 A | * | 3/1981 | Zorgniotti | A61F 7/10 607/104 |
| 4,387,726 A | * | 6/1983 | Denard | A61F 5/453 604/350 |
| 4,453,938 A | | 6/1984 | Brendling | |
| 4,627,846 A | | 12/1986 | Ternstroem | |
| 4,994,051 A | * | 2/1991 | Walsh | A61F 5/453 604/353 |
| 5,275,592 A | * | 1/1994 | Grizzaffi | A61F 5/4401 2/403 |
| 5,342,332 A | | 8/1994 | Wheeler | |
| 5,547,466 A | * | 8/1996 | McRoberts | A61F 5/40 2/403 |
| 5,695,485 A | | 12/1997 | Duperret et al. | |
| 5,807,299 A | * | 9/1998 | McRoberts | A61F 5/40 602/70 |
| 6,059,762 A | | 5/2000 | Boyer et al. | |
| 6,113,582 A | * | 9/2000 | Dwork | A61F 5/453 604/351 |

(Continued)

*Primary Examiner* — Guy K Townsend
(74) *Attorney, Agent, or Firm* — Jason T. Daniel, Esq.; Daniel Law Offices, P.A.

(57) ABSTRACT

A male incontinence device includes a protective sleeve having a plurality of walls that define an interior space. The sleeve includes a first opening at the first end of the sleeve body, and a second opening on the top end of the sleeve body. The first and second openings are selectively closed to secure a male penis within the interior space. The main body includes a moisture wicking interior layer, a moisture absorbing middle layer, and a moisture impermeable outer layer. A belt is provided to engage the waist of a user, and a pair of straps connect the protective sheath to the belt. The device is held in place via the belt and straps, and removal of the penis is prevented via the combination of an adjustable band that is located along the periphery of the first opening, and cooperating structures located along the second opening.

17 Claims, 6 Drawing Sheets

(56) References Cited

U.S. PATENT DOCUMENTS

| | | | |
|---|---|---|---|
| 6,132,412 A * | 10/2000 | Jones | A61F 13/64 |
| | | | 604/392 |
| 6,248,096 B1 * | 6/2001 | Dwork | A61F 5/453 |
| | | | 604/347 |
| 6,443,930 B1 * | 9/2002 | Silverstein | A61F 13/64 |
| | | | 604/353 |
| 6,635,037 B1 | 10/2003 | Bennett | |
| 7,029,178 B2 | 4/2006 | Gzybowski | |
| 8,425,482 B2 * | 4/2013 | Khoubnazar | A61F 13/471 |
| | | | 604/385.09 |
| 8,568,376 B2 * | 10/2013 | Delattre | A61F 13/471 |
| | | | 604/385.01 |
| 8,986,271 B1 * | 3/2015 | Horne | A61F 5/4408 |
| | | | 604/385.09 |
| 9,681,999 B2 * | 6/2017 | Beck | A61F 13/74 |
| 10,307,306 B2 | 6/2019 | Henderson et al. | |
| 2002/0007160 A1 * | 1/2002 | Miskie | A61F 5/453 |
| | | | 604/350 |
| 2002/0177825 A1 * | 11/2002 | Scovel | A61F 5/453 |
| | | | 604/327 |
| 2003/0149409 A1 * | 8/2003 | Lin | A61F 5/453 |
| | | | 604/385.19 |
| 2004/0106909 A1 * | 6/2004 | Browning | A61F 5/453 |
| | | | 604/349 |
| 2006/0229576 A1 | 10/2006 | Conway et al. | |
| 2009/0281510 A1 * | 11/2009 | Fisher | A61F 5/44 |
| | | | 604/351 |
| 2011/0087183 A1 | 4/2011 | Yang | |
| 2019/0021899 A1 * | 1/2019 | Vlet | A61F 2/0009 |
| 2020/0179156 A1 * | 6/2020 | Vlet | A61F 5/453 |

\* cited by examiner

MALE INCONTINENCE DEVICE

TECHNICAL FIELD

The present invention relates generally to the field of incontinence, and more particularly to a male incontinence device.

BACKGROUND

The statements in this section merely provide background information related to the present disclosure and may not constitute prior art.

Male urinary incontinence is the involuntary leakage of urine and can be caused from a variety of factors such as muscular weakness, neurological issues, medical conditions, and age-related factors. Recent studies estimate that over 15 percent of all men suffer from some form of incontinence. As such, there are many known types of commercially available male incontinence devices such as adult diapers, an external catheter, or a sleeve-type collection device.

External catheters typically utilize a tube having an enlarged opening on one end, and a storage container on the other end. Although useful for storing large amounts of urine, a common issue is that it can be quite difficult to position the male penis through the opening due to the malleable nature of the penis. As a result, the penis often becomes misaligned or slips out of the opening during use, thus causing spillage. Moreover, due to the relatively large and bulky nature of such devices, it is exceedingly difficult to use one in an inconspicuous manner, such as at the workplace, for example.

Conversely, sleeve-type incontinence devices typically include a sheet of absorbent material that is directly wrapped around the penis and secured thereon by a rubber band. Although these devices are designed to be inconspicuous, they are only able to hold small amounts of urine (typically between 1-10 ounces) and suffer from several other drawbacks. For example, in order to prevent the device from falling off, the bands must be tightened to an extremely uncomfortable setting. However, as the sleeve receives and stores the urine, it becomes increasingly heavy and slippery, thus causing the sleeve to slide off the penis during use, thus resulting in the same embarrassment noted above with regard to the catheter.

The present invention, directed to a male incontinence device differs from the conventional art in a number of aspects. The manner by which will become more apparent in the description which follows, particularly when read in conjunction with the accompanying drawings.

SUMMARY OF THE INVENTION

The present invention is directed to a male incontinence device. One embodiment of the present invention can include a protective sleeve having a plurality of walls that define an interior space. The sleeve can include a first opening positioned along the first end of the sleeve body, and a second opening that is positioned along the top end of the sleeve body. The first and second openings can be selectively closed so as to secure a male penis within the interior space. The main body can include a layered construction that includes a moisture wicking interior layer, a moisture absorbing middle layer, and a moisture impermeable outer layer.

In one embodiment, the device can include a belt that engages the waist of a user, and a pair of straps that connect the protective sheath to the belt. The device is held in place via the belt and straps, and removal of the penis is prevented via the combination of an adjustable band that is located along the periphery of the first opening, and cooperating structures located along the second opening.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Definitions

As described herein, a "unit" means a series of identified physical components which are linked together and/or function together to perform a specified function.

As described throughout this document, the term "about" "approximately" "substantially" and "generally" shall be used interchangeably to describe a feature, shape, or measurement of a component within a tolerance such as, for example, manufacturing tolerances, measurement tolerances or the like.

As described herein, the term "removably secured," and derivatives thereof shall be used to describe a situation wherein two or more objects are joined together in a non-permanent manner so as to allow the same objects to be repeatedly joined and separated.

As described throughout this document, the term "complementary shape," and "complementary dimension," shall be used to describe a shape and size of a component that is identical to, or substantially identical to the shape and size of another identified component within a tolerance such as, for example, manufacturing tolerances, measurement tolerances or the like.

As described herein, the term "connector" includes any number of different elements that work alone or together to repeatedly join two items together in a nonpermanent manner. Several nonlimiting examples of connectors include, but are not limited to, flexible strips of interlocking projections with a slider (i.e., zipper), thread-to-connect, twist-to-connect, and push-to-connect type devices, opposing strips of hook and loop material (e.g., Velcro®), attractively oriented magnetic elements or magnetic and metallic elements, buckles and compression fittings such as hooks, snaps and buttons, for example. Each illustrated connector and complementary connector can be permanently secured to the illustrated portion of the device via a permanent sealer such as glue, adhesive tape, or stitching, for example.

FIGS. 1-6 illustrate one embodiment of a male incontinence device 10 that are useful for understanding the inventive concepts disclosed herein. In each of the drawings, identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

Figure 1:
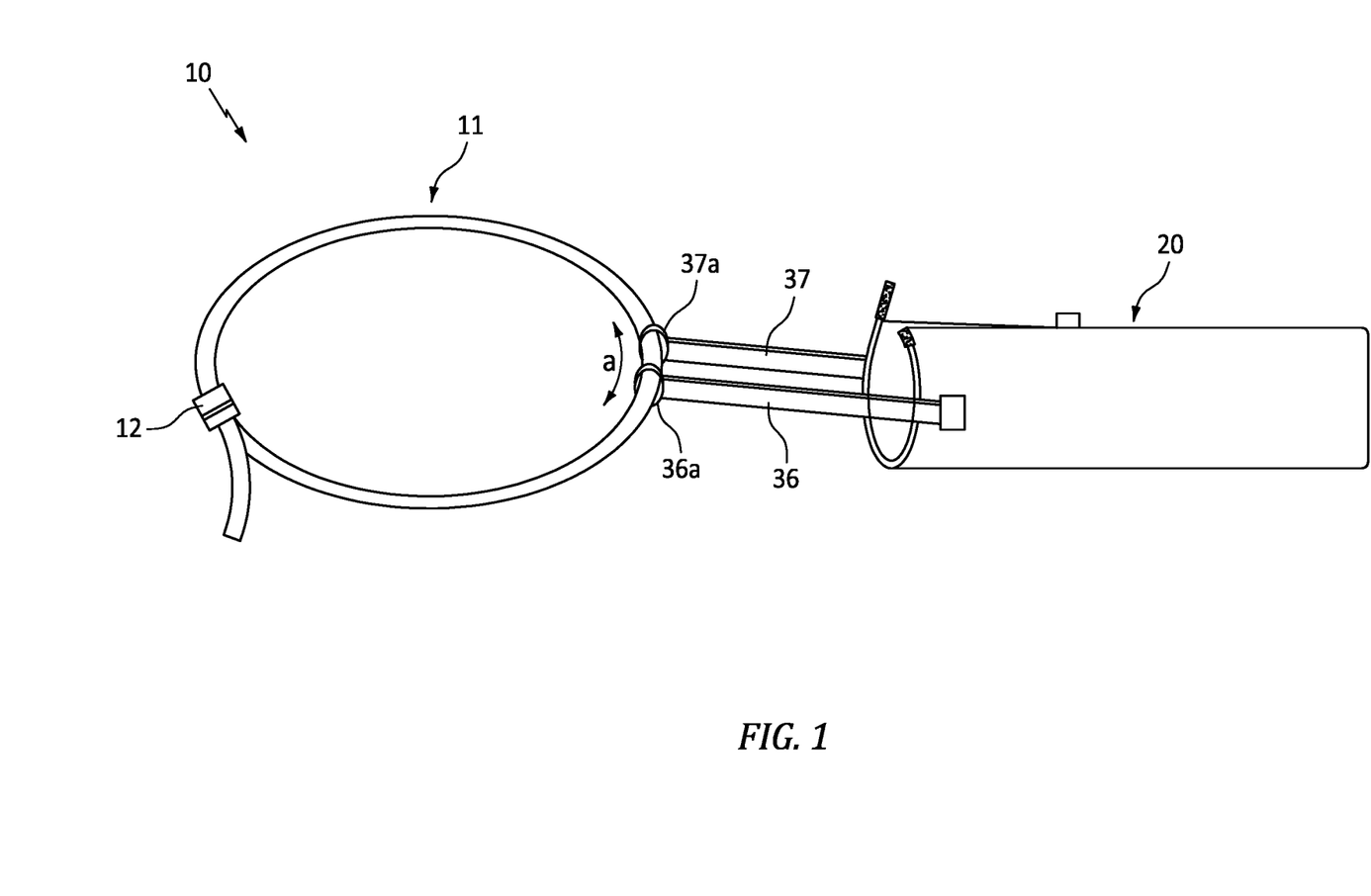
FIG. 1 is a perspective view of a male incontinence device that is useful for understanding the inventive concepts disclosed herein.

As shown at FIG. 1, the device 10 can include, essentially, an elongated belt 11 that is connected to a protective sleeve 20 via a pair of elastomeric straps 35 and 36.

The belt 11 can function to secure the device about the waist of a user. In this regard, the belt can be manufactured in any number of different lengths and widths so as to be used by individuals of varying body shapes and sizes. In the preferred embodiment, the belt will be constructed from a lightweight and malleable material such as nylon, for example, and can include a length adjustment mechanism 12 such as the illustrated plastic lock slider buckle.

Although described above with regard to a particular construction material and type of buckle, this is for illustrative purposes only. To this end, the belt may be constructed from any number of other materials such as various thermoplastics, fabrics and/or natural materials such as leather, for example. Likewise, the adjustment mechanism may include any number of other types of buckles capable of allowing a user to adjust the length of the belt. Moreover, other embodiments are contemplated wherein the belt is constructed from an elastomeric material so as to be stretchable in nature. In such an embodiment, the belt may be provided with or without the length adjustment mechanism.

Figure 2:
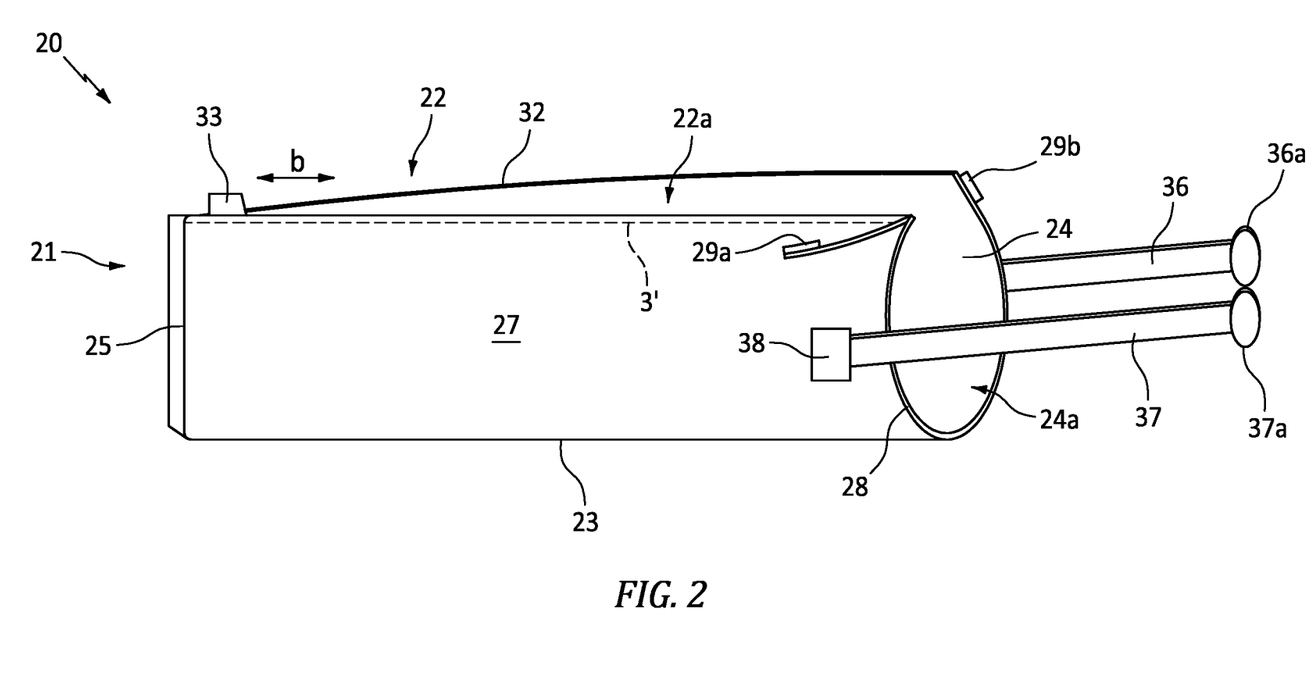
FIG. 2 is a side view of the protective sleeve of the male incontinence device, in accordance with one embodiment of the invention.
Figure 3:
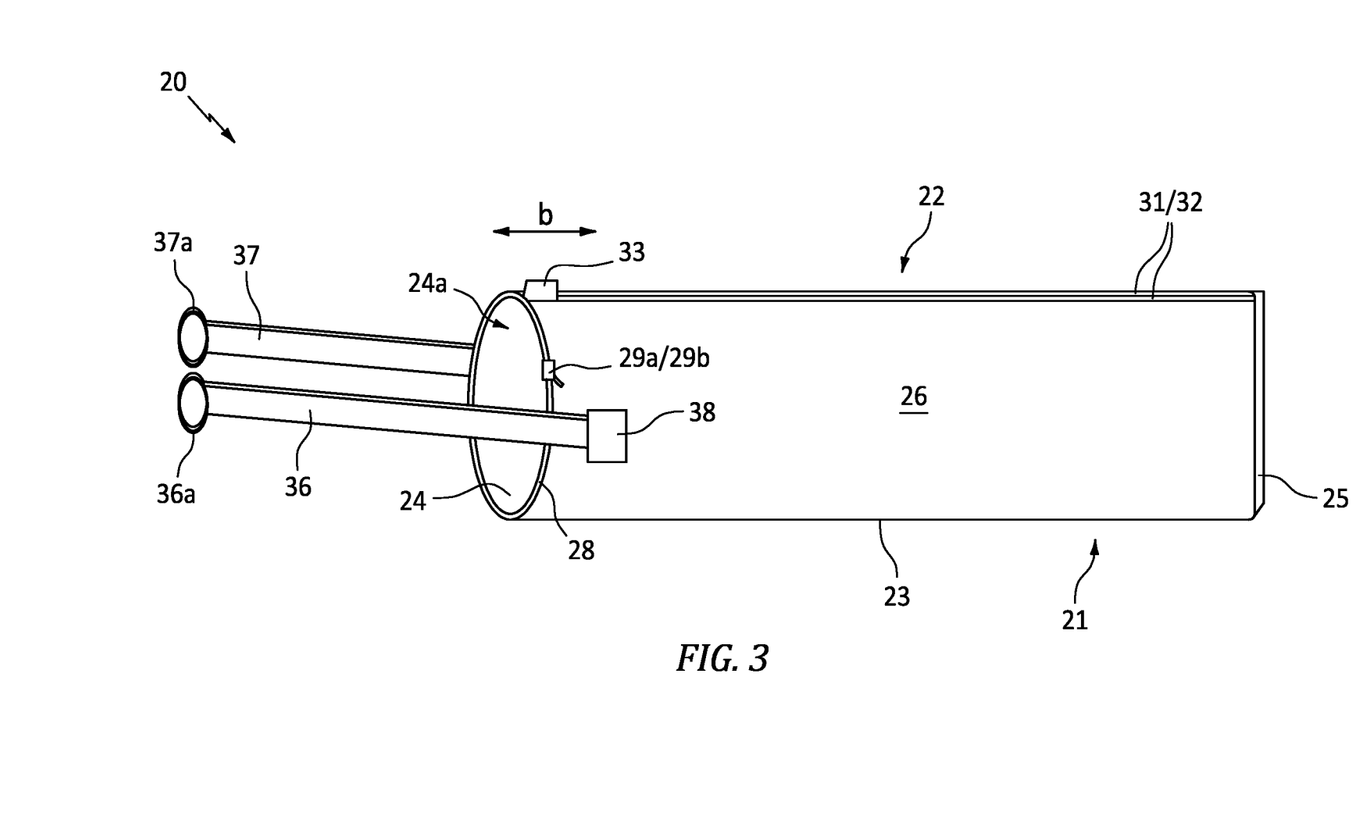
FIG. 3 is another side view of the protective sleeve of the male incontinence device, in accordance with one embodiment of the invention.

FIGS. 2 and 3 illustrate one embodiment of the protective sleeve 20 that includes a main body 21 having a top end 22, a bottom end 23, a front end 24, a back end 25 and a pair of side walls 26 and 27 that define an interior space.

As shown, the front end of the sleeve body can include an opening 24a that is encompassed by an attachment band 28. In the preferred embodiment, the attachment band can be constructed from an elastomeric material and can have connectors 29a and 29b, such as strips of hook and loop material, for example, along each end. The connectors can function to selectively join the ends of the band together to form a circle having any number of different diameters.

In one embodiment, the top end of the main body can include an opening 22a along the length thereof. The opening can be defined by the upper ends of each of the sidewalls 26 and 27 which can include cooperating coupling structures 31 and 32 that can be selectively joined together via a slider 33. Such a feature allows a user to move the slider along the length of the coupling structures (see arrow b) to selectively open and close the top of the body as shown at FIGS. 2 and 3, respectively. One example of a suitable combination of cooperating coupling structures and slider for use herein is described in U.S. Pat. No. 7,029,178 to Gybowski, the contents of which are incorporated herein. However, any number of other types of connectors for selectively opening and closing the opening 22a are also contemplated for use herein.

In one embodiment, a pair of elongated straps 36 and 37 can extend outward from the sidewalls 26 and 27, respectively, of the protective sleeve body. As shown, each of the straps can include a first end that is secured onto the sleeve body 21 via connectors 38 such as glue, for example, and a second end having loops 36a and 37a, along the respective ends. As shown by arrow a of FIG. 1, the loops can removably engage the belt 11 in order to allow the sleeve to slide along the length of the belt so as to allow a user to position the sleeve in any number of locations and orientations—both horizontal and vertical—relative to the belt when the belt is worn about the waist of a user.

In the preferred embodiment, each of the straps 36 and 37 will be constructed from an elastomeric material. As will be described below, the belt and straps function to align and secure the device adjacent to the penis of a user. As such, by providing the ability for the straps to expand and contract, the sheath will be able to move naturally toward and away from the user's body as the user does everyday activities such as walk, sit, or lie down. As such, the elastic nature of the straps is an important feature for ensuring the sheath remains in contact with the user at all times.

In the preferred embodiment, the sleeve body can include a layered construction wherein each layer performs a different and specific function. As illustrated in cross sectional drawing of FIG. 4, the sleeve body 21 can preferably include an inside facing layer 41, a middle layer 42 and an outside facing layer 43.

Figure 4:
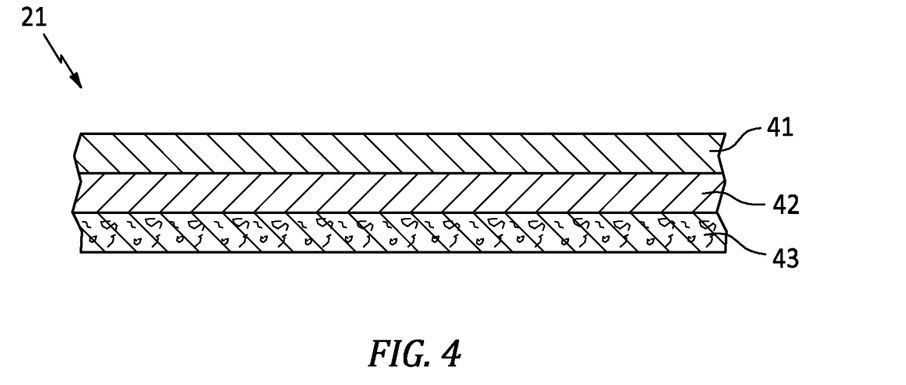
FIG. 4 is a partial cutout cross section view of the layered construction of the sleeve body of the male incontinence device, in accordance with one embodiment of the invention.

The inside facing layer 41 can comprise or line the interior surfaces of the main body walls that define the interior space of the sheath body. As such, the inside facing layer will be in direct contact with the users penis when using the device 10 as will be described below. In one embodiment, the inside facing layer 41 can be constructed from a soft, malleable and moisture wicking fabric such as Polyester, Polypropylene, Wool, Micromodal fabric or bamboo, among others, for example, that actively draws moisture away from the body.

In the preferred embodiment, the inside facing layer will also include an antibacterial coating. Of course, any number of other types of materials that can function to draw moisture from the penis into the middle layer and that are suitable for direct contact with the human body are also contemplated.

The middle layer 42 can function to absorb and retain urine that passes through the inside layer 41. In the preferred embodiment, the middle layer can be constructed from a malleable liquid-absorbing material such as sodium polyacrylate gel beads, for example, however any number of other materials capable of absorbing and retaining liquids such as various other absorbing polymers and natural materials are also contemplated for use herein.

The outside facing layer 43 can be constructed from a malleable and liquid impermeable material such as laminated natural or synthetic fabrics, polyvinyl chloride (PVC), polyurethane (PU), silicone elastomer, fluoropolymers, or other such materials that do not permit liquid to pass therethrough and that are safe for prolonged contact with human skin. The outside facing layer can function to contain the liquids absorbed by the middle layer and to ensure the same does not leak.

Additionally, the outside layer will provide a thermal barrier so as to prevent the warmth of fresh urine and the coldness of stored urine from being belt by the user when the outside of the main body is resting against the user's leg. This thermal barrier will ideally be formed by the arrangement of the above noted materials; however, some embodiments are contemplated wherein the thermal barrier is created by another layer of thermal isolative material (e.g., cotton cloth, foam, etc.,) that is located along the exterior of the outside layer, thus creating a fourth layer.

In one embodiment, the sleeve body can be manufactured as a unitary component such that each of the layers 41, 42 and 43 are not separable. However, other embodiments are contemplated wherein the main body is constructed modularly, such that one or both of the inside layer 41 and middle layer 42 are removably positionable inside the outside layer 43. Such a feature allows a user to reuse the main body and replace the inner moisture wicking and absorbent layers as needed.

Although described above with respect to a particular material(s), and three layers, this is for illustrative purposes only. To this end, those of skill in the art will recognize that the protective sleeve body can be constructed utilizing any number of different layers and/or materials, without limitation, that are capable of performing the functionality described herein.

Figure 5:
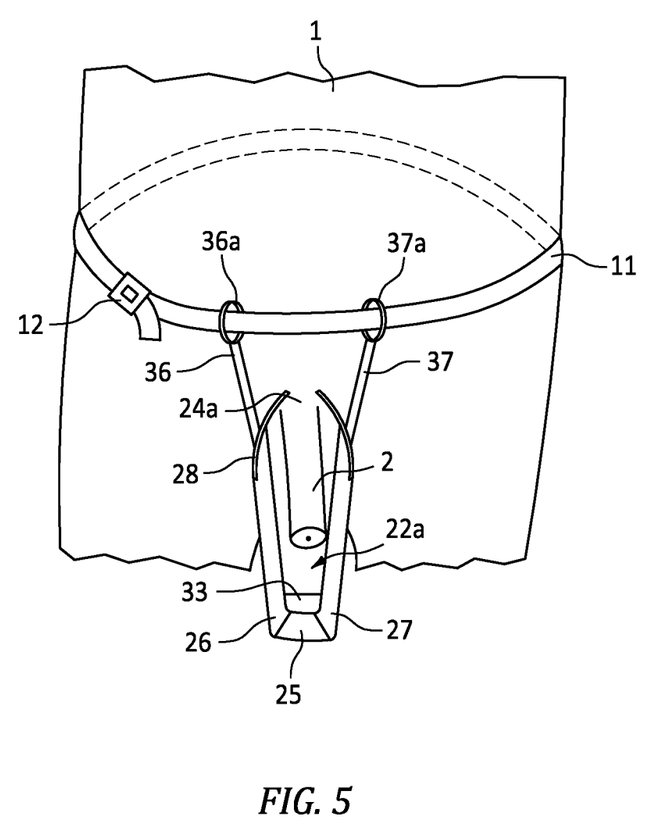
FIG. 5 is a front view of the male incontinence device in operation, in accordance with one embodiment of the invention.
Figure 6:
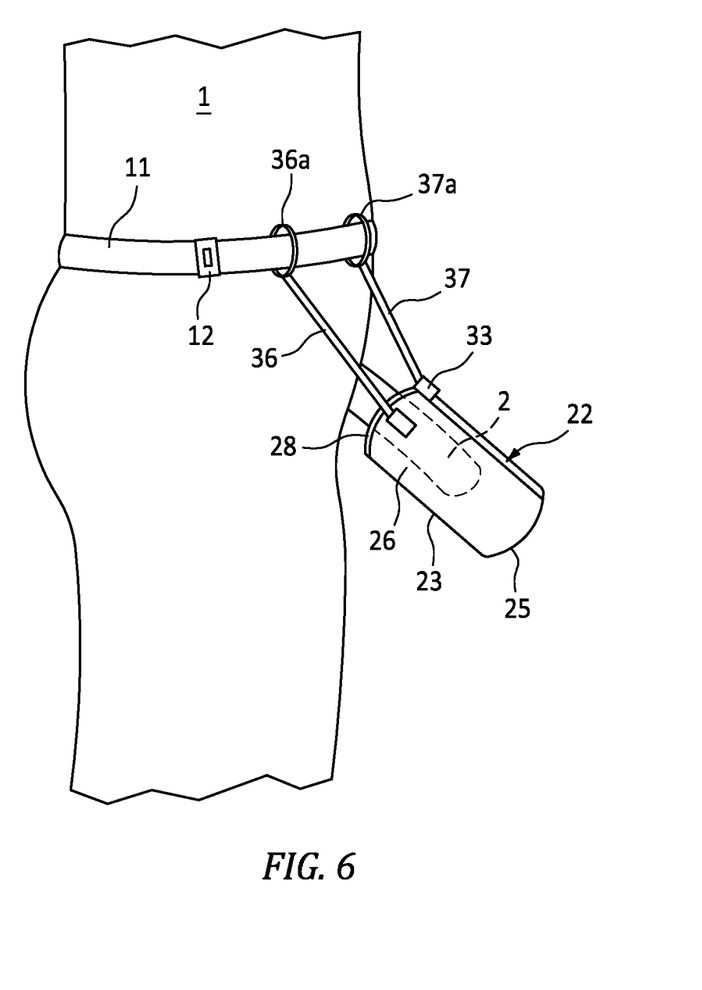
FIG. 6 is a side view of the male incontinence device in operation, in accordance with one embodiment of the invention.

FIGS. 5 and 6 illustrate one embodiment of the device 10 in operation. As shown, a user 1 can properly wear the device by first positioning the belt 11 about their waist and adjusting the same to position the sheath beneath their penis 2. When so positioned, the user is able to completely insert the penis both vertically and horizontally within the interior space of the main body via openings 22a and 24a, respectively. Next, the user can adjust and secure the ends of the band 28 together in order to tightly engage the shaft of the penis, thus preventing the same from sliding out of the opening 24a. Finally, the user can move the slider 33 toward their body to close the upper opening 22a, thus fully enclosing the penis 2 within the sheath body.

Once installed, the belt and straps work to maintain the sheath against the body of the user and in alignment with the user's penis at all times. Additionally, the band and slider ensure the penis remains securely positioned within the interior space of the sheath, thus preventing the same from sliding out. When so positioned, urine leaking from the penis will be actively wicked away from the user's skin and captured by the absorbent layer. The urine will be stored by the absorbent layer and will not leak due to the non-permeable nature of the outer layer of the sheath body.

Accordingly, the above described device provides a novel male incontinence device that is not rendered obvious by any known art.

As to a further description of the manner and use of the present invention, the same should be apparent from the above description. Accordingly, no further discussion relating to the manner of usage and operation will be provided.

As described herein, one or more elements of the device 10 can be secured together utilizing any number of known attachment means. Moreover, although the above embodiments have been described as including separate individual elements, the inventive concepts disclosed herein are not so limiting. To this end, one of skill in the art will recognize that one or more individually identified elements may be formed together as one or more continuous elements, either through manufacturing processes, or through the use of a singular piece of material milled or machined with the aforementioned components forming identifiable sections thereof.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Likewise, the term "consisting" shall be used to describe only those components identified. In each instance where a device comprises certain elements, it will inherently consist of each of those identified elements as well.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device, comprising:
 a protective sleeve comprising a main body having a top end, a bottom end, a front end, a back end and a pair of sides that define an interior space,
 said sleeve further comprising a first opening that is positioned along the front end of the sleeve, and an adjustable band that is positioned adjacent to the first opening,
 said sleeve further comprising a second opening that is positioned along the top end of the sleeve and a connector that is positioned adjacent to the second opening;
 a pair of straps that extend outward from the pair of sides of the protective sleeve; and
 a belt that is connected to the pair of straps,
 wherein the belt and the pair of straps are configured to position the protective sleeve about the waist of a user, and
 wherein the first opening and the second opening are each configured to simultaneously receive a penis of a user,
 wherein the adjustable band is configured to engage and be tightened against a shaft of the received penis, and wherein the connector is configured to secure the second opening in a closed position with the received penis located within the interior space of the sleeve.

2. The device of claim 1, wherein the main body further includes layers configured to absorb and store urine from the penis within the interior space.

3. The device of claim 1, wherein the main body includes a layered construction.

4. The device of claim 3, wherein the layered construction further includes an inside layer that is constructed from a moisture wicking material.

5. The device of claim 4, wherein the layered construction further includes a middle layer that is constructed from a liquid absorbing material.

6. The device of claim 5, wherein the layered construction further includes an outside layer that is constructed from a liquid impermeable material.

7. The device of claim 6, wherein each of the inside layer, the middle layer and the outside layer are permanently secured together.

8. The device of claim 6, wherein at least one of the inside layer or the middle layer are removably positioned within the outside layer.

9. The device of claim 1, wherein the belt includes an adjustment mechanism.

10. The device of claim 1, wherein each of the pair of straps include a loop along a distal end, and each of the loops are configured to slidingly engage the belt.

11. The device of claim 10, wherein each of the pair of straps are constructed from an elastomeric material.

12. The device of claim 1, wherein the adjustable band further includes a first end that is connected to one of the pair of sides of the sleeve, and a second end that is connected to the other of the pair of sides of the sleeve.

13. The device of claim 12, wherein the first end of the adjustable band includes a first band connector and the second end of the adjustable band includes a second band connector.

14. The device of claim 13, wherein the first end of the adjustable band is configured to be selectively connected to the second end of the adjustable band by an engagement of the first band connector and the second band connector.

15. The device of claim 14, wherein each of the first band connector and the second band connector comprise strips of hook and loop material.

16. The device of claim 1, wherein the second opening extends along an entire length of the top end of the sleeve.

17. The device of claim 16, wherein the connector comprises:
   a first cooperating structure that is positioned on one of the pair of sides of the sleeve;
   a second cooperating structure that is positioned on the other of the pair of sides of the sleeve; and
   a slider that is slidingly engaged with each of the first cooperating structure and the second cooperating structure.

* * * * *